United States Patent
Daly

(10) Patent No.: US 10,576,275 B2
(45) Date of Patent: Mar. 3, 2020

(54) SYSTEM AND METHOD FOR CONFIGURING AN EXTERNAL DEVICE USING OPERATING PARAMETERS FROM AN IMPLANTED DEVICE

(75) Inventor: Christopher Newton Daly, Bilgola Plateau (AU)

(73) Assignee: Cochlear Limited, Macquarie University, NSW (AU)

( * ) Notice: Subject to any disclaimer, the term of this patent is extended or adjusted under 35 U.S.C. 154(b) by 1629 days.

(21) Appl. No.: 12/401,600

(22) Filed: Mar. 10, 2009

(65) Prior Publication Data

US 2010/0016922 A1 Jan. 21, 2010

Related U.S. Application Data

(63) Continuation-in-part of application No. 10/333,676, filed as application No. PCT/AU01/00811 on Jul. 6, 2001, now Pat. No. 7,502,653.

(51) Int. Cl.
| | |
|---|---|
| *A61N 1/36* | (2006.01) |
| *A61N 1/08* | (2006.01) |
| *A61N 1/372* | (2006.01) |
| *G16H 40/63* | (2018.01) |

(52) U.S. Cl.
CPC ........... *A61N 1/08* (2013.01); *A61N 1/37252* (2013.01); *G16H 40/63* (2018.01); *A61N 1/36036* (2017.08)

(58) Field of Classification Search
USPC ............................................. 607/31, 57, 61
See application file for complete search history.

(56) References Cited

U.S. PATENT DOCUMENTS

| | | | |
|---|---|---|---|
| 4,532,930 A | 8/1985 | Crosby et al. | |
| 4,776,322 A * | 10/1988 | Hough et al. | ................. 381/326 |
| 5,569,307 A | 10/1996 | Schulman et al. | |

(Continued)

FOREIGN PATENT DOCUMENTS

| | | |
|---|---|---|
| DE | 19915846 | 8/2000 |
| EP | 0730882 | 9/1996 |

(Continued)

OTHER PUBLICATIONS

International Search Report. PCT/AU01/00811; Filed Jul. 6, 2001; dated Sep. 10, 2001.

(Continued)

*Primary Examiner* — Michael W Kahelin
(74) *Attorney, Agent, or Firm* — Piloff Passino & Cosenza LLP; Martin J. Cosenza

(57) ABSTRACT

According to one aspect of the present invention, there is provided an implantable medical device comprising: an implantable component, comprising an implantable memory module, configured to receive and store recipient-specific operating parameters in the implantable memory module, an external component, comprising an external memory module, configured to communicate with the implantable component to receive the recipient-specific operating parameters, and to configure the external component using the recipient-specific operating parameters, wherein the implantable medical device is configured to transfer the recipient-specific operating parameters upon operationally coupling the implantable component with the external component.

22 Claims, 11 Drawing Sheets

(56) References Cited

U.S. PATENT DOCUMENTS

| | | |
|---|---|---|
| 5,571,148 A | 11/1996 | Loeb et al. |
| 5,690,690 A | 11/1997 | Nappholz et al. |
| 5,800,473 A | 9/1998 | Faisandier |
| 5,817,137 A | 10/1998 | Kaemmerer |
| 5,891,180 A | 4/1999 | Greeninger et al. |
| 5,941,905 A | 8/1999 | Single |
| 6,195,585 B1 | 2/2001 | Karunasiri et al. |
| 6,198,971 B1 | 3/2001 | Leysieffer |
| 6,219,580 B1 * | 4/2001 | Faltys et al. ............... 607/57 |
| 6,243,608 B1 | 6/2001 | Pauly et al. |
| 6,285,909 B1 * | 9/2001 | Sweeney et al. ............ 607/32 |
| 6,308,099 B1 * | 10/2001 | Fox et al. ................... 607/31 |
| 6,327,501 B1 | 12/2001 | Levine et al. |
| 6,390,971 B1 * | 5/2002 | Adams et al. ............... 600/25 |
| 6,443,891 B1 | 9/2002 | Grevious |
| 6,482,154 B1 * | 11/2002 | Haubrich et al. .......... 600/300 |
| 6,537,200 B2 | 3/2003 | Leysieffer et al. |
| 6,553,263 B1 * | 4/2003 | Meadows et al. ............ 607/61 |
| 6,565,503 B2 | 5/2003 | Leysieffer et al. |
| 6,575,894 B2 | 6/2003 | Leysieffer et al. |
| 6,697,674 B2 | 2/2004 | Leysieffer |
| 6,738,670 B1 * | 5/2004 | Almendinger et al. ....... 607/60 |
| 6,740,075 B2 | 5/2004 | Lebel et al. |
| 7,346,397 B2 | 3/2008 | Money et al. |
| 7,502,653 B2 | 3/2009 | Daly |
| 2004/0024429 A1 | 2/2004 | Daly |
| 2004/0176822 A1 | 9/2004 | Thompson et al. |
| 2006/0020304 A1 | 1/2006 | Torgerson et al. |
| 2009/0306742 A1 | 12/2009 | Van Dijk et al. |
| 2010/0016922 A1 | 1/2010 | Daly |

FOREIGN PATENT DOCUMENTS

| | | |
|---|---|---|
| WO | 0072917 | 12/2000 |
| WO | 01/03622 | 1/2001 |
| WO | 01/06810 | 1/2001 |
| WO | 01/13991 | 3/2001 |
| WO | WO 2003/003956 | 1/2003 |
| WO | WO 2003/009207 | 1/2003 |

OTHER PUBLICATIONS

European Search Report. EP 01 95 1205. dated Mar. 31, 2005.
EPO Official Communication. EP 01 951 205.2. dated Jan. 23, 2008.
EPO Official Communication. EP 01 951 205.2. dated Feb. 2, 2006.
EPP Official Communication. EP 01 951 205.2. dated Sep. 14, 2006.
International Search Report. PCT/AU2007/000142; dated May 2, 2007.
Japanese Office Action; JP 2003-509972; dated Jun. 29, 2010.

* cited by examiner

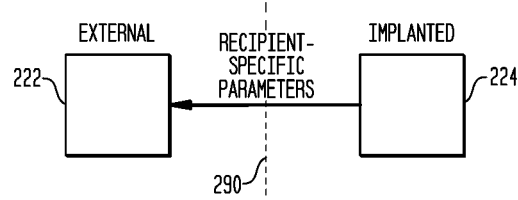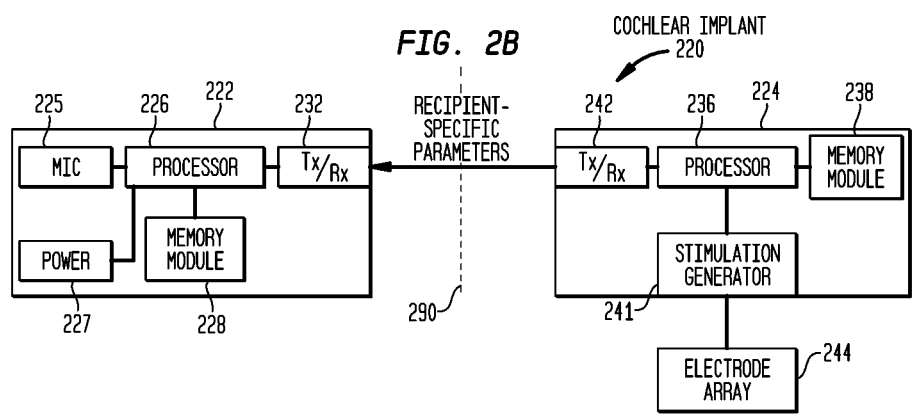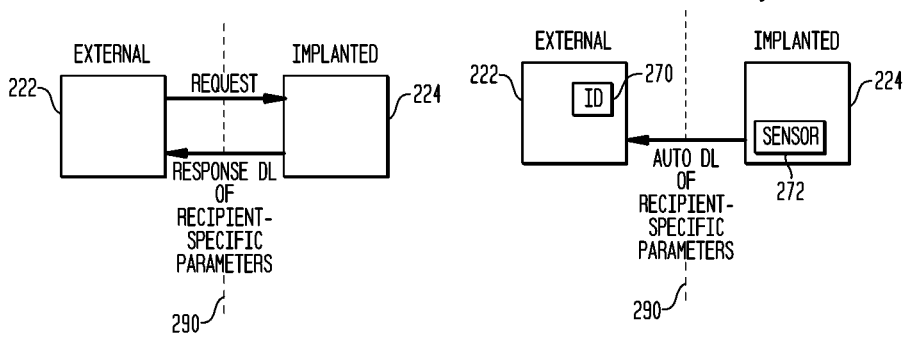

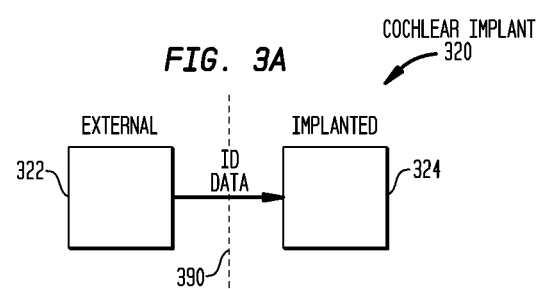
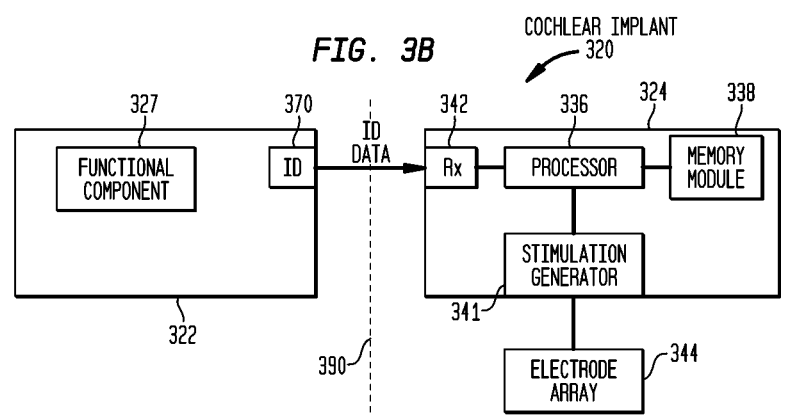

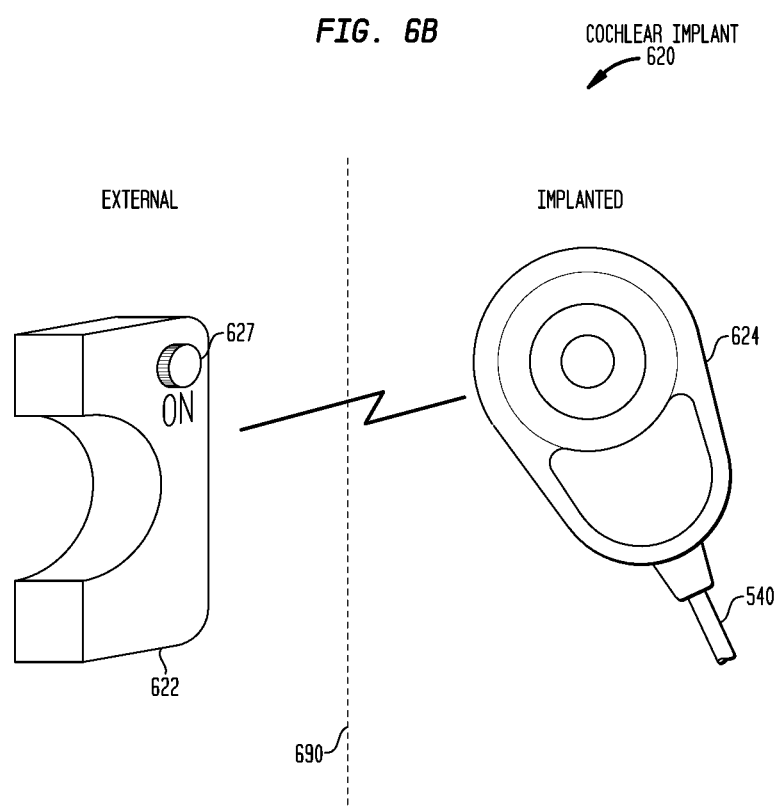

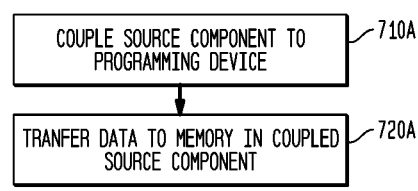
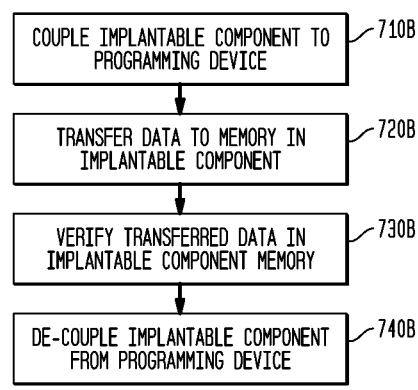

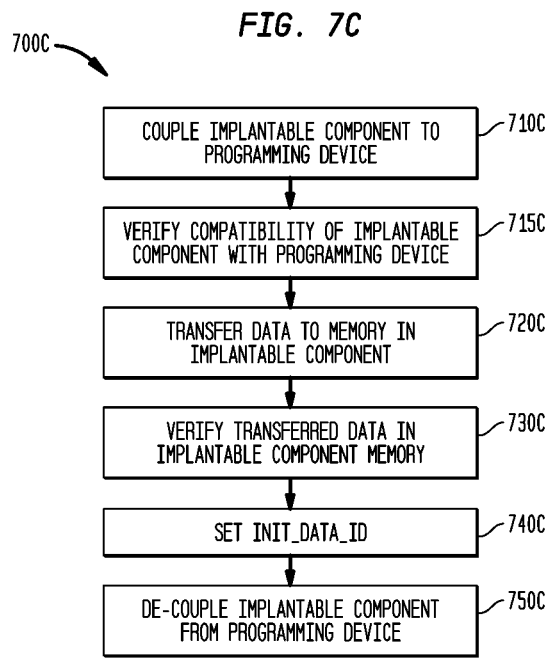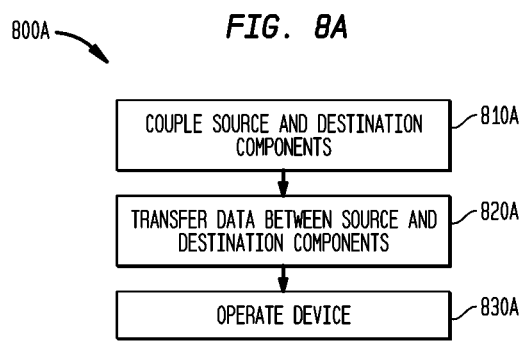

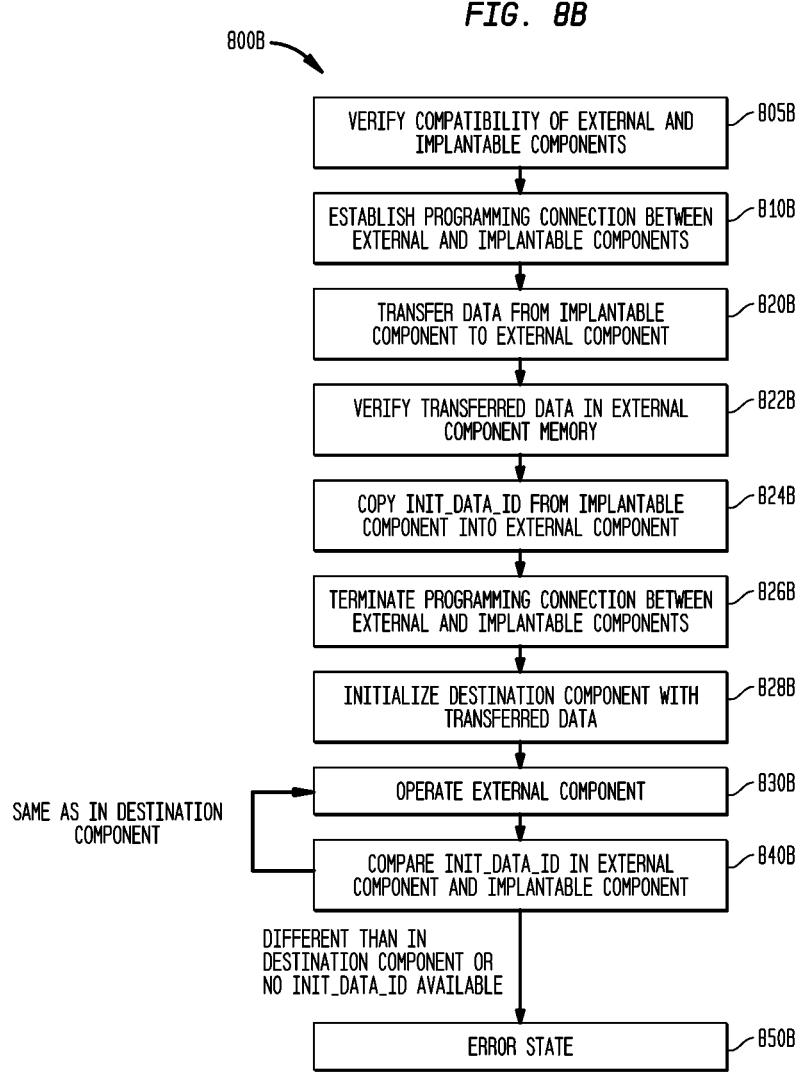

SYSTEM AND METHOD FOR CONFIGURING AN EXTERNAL DEVICE USING OPERATING PARAMETERS FROM AN IMPLANTED DEVICE

CROSS-REFERENCE TO RELATED APPLICATIONS

This application is a continuation-in-part application of U.S. patent application Ser. No. 10/333,676 entitled "Configuration of Implanted Devices," filed Jul. 6, 2001, now U.S. Pat. No. 7,502,653, which is a National Stage Application of PCT/AU01/00811 filed Jul. 6, 2001, all of which are hereby incorporated by reference herein.

BACKGROUND

Field of the Invention

The present invention relates generally to implantable medical devices, and more particularly, to the configuration of implantable medical devices.

Related Art

Implantable medical devices have become more commonplace as their therapeutic benefits become more widely accepted and the impact and risk of their use have been managed. Many such medical devices include one or more implantable components, collectively referred to as an implantable assembly, and one or more external components, collectively referred to as an external assembly.

In some devices, the external and implanted components are communicably linked by a communication link, such as an RF or inductive link, to provide the required functionality. Although the following will often refer to a particular category of implantable medical devices, namely implantable prosthetic hearing devices known as cochlear implants, it is to be understood that the following is applicable to other types of implantable medical devices such as spinal, visual or other neural stimulators, and medical devices developed for other applications, including those medical implant applications which help to diagnose, monitor, regulate or treat conditions within a recipient's body in which components of the medical device is implanted.

Within the context of prosthetic hearing devices, such implantable medical devices may be beneficially used to treat hearing loss. Hearing loss is generally of two types, conductive and sensorineural. The treatment of both types of hearing loss has been quite different, relying on different principles to enable sound percepts to be generated in a recipient's brain. Conductive hearing loss occurs when the normal mechanical pathways for sound to reach the hair cells in the cochlea are impeded, for example, by damage to the ossicles. In such recipients, hearing is often improved with the use of conventional hearing aids. Such hearing aids amplify sound so that acoustic information reaches the hair cells of the cochlea. Typically, conventional hearing aids utilize acoustic mechanical stimulation, whereby the sound is amplified according to a number of varying techniques, and delivered to the inner ear as mechanical energy. This may be, for example, through a column of air to the eardrum, or through direct delivery to the ossicles of the middle ear.

Sensorineural hearing loss is due to the absence or destruction of the cochlear hair cells which are needed to transduce acoustic signals into auditory nerve impulses. Individuals suffering from this type of hearing loss are unable to derive any benefit from conventional hearing aids regardless of the magnitude of the acoustic mechanical stimulus. In such cases, Cochlear™ implants (also referred to as Cochlear™ devices, Cochlear™ prostheses, Cochlear™ implant systems, and the like; simply "cochlear implants" herein) have been developed to provide hearing percepts in such individuals. Cochlear implants provide electrical stimulation via stimulating electrodes positioned as close as possible to the nerve endings of the auditory nerve, essentially bypassing the cochlear hair cells. The application of a stimulation pattern to the nerve endings causes impulses to be sent to the brain via the auditory nerve, resulting in the brain perceiving the impulses as sound.

Conventional cochlear implants employ one or more implanted components as well as one or more external components. External components include, for example, a microphone and a speech processor. Internal components include, for example, an electrode carrier member for implantation in the cochlea to position an array of electrodes or contacts in the cochlea, and a stimulator unit which generates and delivers electrical stimulation signals to the electrodes.

In conventional medical devices, including the conventional cochlear implants noted above, one or more of the external components are typically configured, or customized, for operation with a specific recipient. Such customization is typically achieved by deriving a set of instructions or settings values for that recipient, referred to as recipient-specific operating parameters, and storing those parameters in the customizable external component. The recipient-specific operating parameters are then used by the external component to perform operations for that recipient. In the cochlear implant application introduced above, such operations include, for example, processing received sounds in a specific manner that is optimized or "fitted" for the particular recipient. For cochlear implants, these settings values or instructions are typically set by audiologists, surgeons or other health care professional around the time that the cochlear implant is implanted in the recipient, or after allowing time for healing or adjustment to pass following implantation of the cochlear implant in the recipient.

SUMMARY

According to one aspect of the present invention, there is provided an implantable medical device, the device comprising: an implantable component, comprising an implantable memory module, configured to receive and store recipient-specific operating parameters in the implantable memory module, an external component, comprising an external memory module, configured to communicate with the implantable component to receive the recipient-specific operating parameters, and to configure the external component using the recipient-specific operating parameters, wherein the implantable medical device is configured to transfer the recipient-specific operating parameters upon operationally coupling the implantable component with the external component.

According to another aspect of the present invention, there is provided a method for configuring an implantable medical device for a recipient having an implantable component and an external component, each of the components having a respective implantable memory module and external memory module, the method comprising: storing recipient-specific operating parameters in the implantable component, communicably coupling the implantable component and the external component, transferring the recipient-specific operating parameters from the implantable component to the external component, and configuring the external component by applying the recipient-specific operating parameters to the external component.

According to a further aspect of the present invention, there is provided a computer readable medium comprising a computer program for controlling a processor to execute a method for configuring an implantable medical device for a recipient having an implantable component and an external component, each of the components having a respective implantable memory module and external memory module, the method comprising: storing recipient-specific operating parameters in the implantable component, communicably coupling the implantable component and the external component, transferring the recipient-specific operating parameters from the implantable component to the external component, and configuring the external component by applying the recipient-specific operating parameters to the external component.

According to a yet further aspect of the present invention, there is provided an implantable medical device for a recipient having an implantable component and an external component, each of the components having a respective implantable memory module and external memory module, the device comprising: means for storing recipient-specific operating parameters in the implantable component, means for communicably coupling the implantable component and the external component, means for transferring the recipient-specific operating parameters from the implantable component to the external component, and means for configuring the external component by applying the recipient-specific operating parameters to the external component.

According to another aspect of the present invention, there is provided an implantable medical device, the medical device comprising: an implantable component, comprising an implantable memory module, configured to receive and store recipient-specific operating parameters in the implantable memory module, an external component, comprising an external memory module, configured to communicate with the implantable component to transmit configuration data to or from the implantable component, wherein the implantable medical device is configured to transfer the configuration data upon operationally coupling the implantable component with the external component.

BRIEF DESCRIPTION OF THE DRAWINGS

Embodiments of the present invention are described below with reference to the attached drawings, in which:

FIG. 2A is a functional block diagram of a cochlear implant according to embodiments of the present invention in which internally-stored recipient-specific operating parameters is transmitted to an external component;

FIG. 2B is a functional block diagram of a cochlear implant according to embodiments of the present invention in which internally-stored recipient-specific operating parametersis transmitted to an external component;

FIG. 2C is a functional block diagram of a cochlear implant according to embodiments of the present invention in which internally-stored recipient-specific operating parameters are transmitted to an external component in response to a request generated by the external component;

FIG. 2D is a functional block diagram of a cochlear implant according to embodiments of the present invention in which internally-stored recipient-specific operating parameters are transmitted to an external component automatically;

FIG. 3A is a functional block diagram of a cochlear implant according to embodiments of the present invention in which externally-stored data is received by an implanted component;

FIG. 3B is a functional block diagram of a cochlear implant according to embodiments of the present invention in which externally-stored data is received by an implanted component;

FIG. 6B is a simplified perspective view of an external and implantable components of a cochlear implant according to embodiments of the present invention;

FIG. 7A is a flowchart of the initial customization or programming of a cochlear implant according to embodiments of the present invention;

FIG. 7B is a flowchart of the initial customization or programming of a cochlear implant according to other embodiments of the present invention;

FIG. 7C is a flowchart diagram of the initial programming of a cochlear implant according to embodiments of the present invention;

FIG. 8A is a flowchart of the programming 800A of a destination component from a source component of a cochlear implant according to embodiments of the present invention;

FIG. 8B is a flowchart of the programming 800B of a destination component from a source component of a cochlear implant according to other embodiments of the present invention;

DETAILED DESCRIPTION

Figure 1:
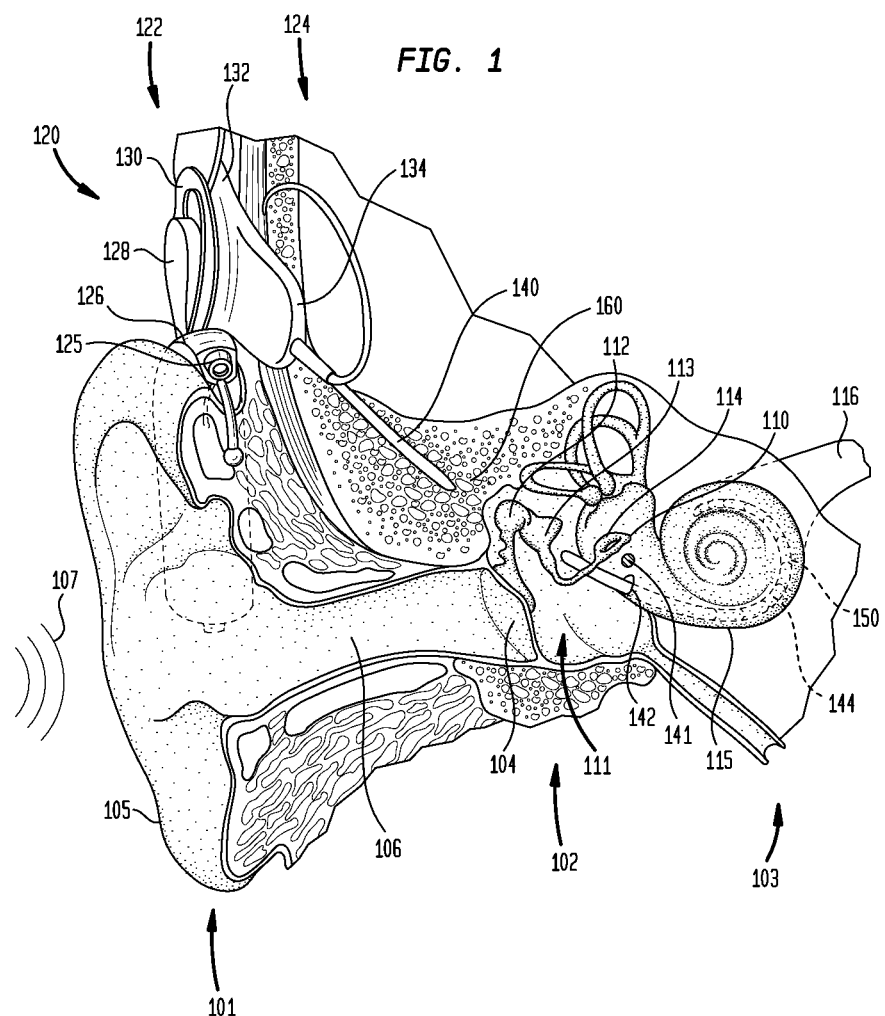
FIG. 1 is a perspective view of an example of a cochlear implant suitable for implementing embodiments of the present invention.

Embodiments of the present invention are generally directed to the configuration of a customizable external component of an implantable medical device. The parameters, which when used by the customizable external component cause it to operate for the specific recipient, are stored in an implantable component of the device. Such parameters are provided to the customizable external component, for example when the external and internal components are operationally coupled, when the medical device is initially powered, or at some other occasion in which the interoperability of the external and internal components is to be established and or confirmed so that the medical device may perform operations for this specific recipient.

Medical devices having customizable external components which are configured for a specific recipient utilizing date stored within a component implanted in the recipient enables, for example, for the replacement of the external component by the recipient without further contribution by a audiologist, doctor, surgeon or other health care professional.

According to embodiments of the present invention, the external components are generic in that they are provided to the recipient without first setting any operational parameters that are tailored for use by the particular recipient. The configuration process involves storing operational parameters that are specific to a particular recipient in the memory module of an implantable component, transmitting at least one configuration data between the implantable and external components, and changing or confirming the configuration of at least one of the implantable and external components based on the transferred configuration data.

Cochlear implants use direct electrical stimulation of auditory nerve cells to bypass absent or defective hair cells that normally transduce acoustic vibrations into neural activity. Such devices generally use multi-contact electrodes inserted into the scala tympani of the cochlea so that the electrodes may differentially activate auditory neurons that normally encode differential pitches of sound. These devices are also used to treat a smaller number of recipients with bilateral degeneration of the auditory nerve. Such devices are described in commonly owned and co-pending U.S. patent application Ser. Nos. 11/605,952 and 11/605,951, which are hereby incorporated by reference herein. For such recipients, a cochlear implant provides stimulation of the cochlear nucleus in the brainstem. Such devices, therefore, are commonly referred to as auditory brainstem implants (ABIs).

Although some embodiment of the present invention are described herein with reference to a particular type of cochlear implant, it should be understood that embodiments of the present invention may be implemented in connection with all forms of cochlear implants. Furthermore, it should be understood by those of ordinary skill in the art that embodiments of the present invention may be implemented in stimulating medical devices other than cochlear implants such as neurostimulators, cardiac pacemakers/defibrillators, etc. as well as other medical devices which utilize a carrier member to temporarily or permanently implant, deliver or otherwise introduce into a recipient a therapeutic agent, sensor, electrodes or other active or passive components now or later developed.

Exemplary embodiments of a cochlear implant utilized in accordance with embodiments of the present invention include a Contour™, Freedom™, Nucleus™ or Cochlear™ implant sold by Cochlear Limited, Australia. Such devices are described in U.S. Pat. Nos. 4,532,930, 6,537,200, 6,565,503, 6,575,894, and 6,697,674, which are hereby incorporated by reference herein. Similarly, cochlear implants utilizing a short electrode array are described in commonly owned and co-pending U.S. patent application Ser. Nos. 11/605,952 and 11/605,951, which are hereby incorporated by reference herein.

FIG. 1 is a cut-away view of the relevant components of outer ear 101, middle ear 102 and inner ear 103, with an exemplary cochlear implant 120. In a fully functional ear, outer ear 101 comprises an auricle 105 and an ear canal 106. An acoustic pressure or sound wave 107 is collected by auricle 105 and channeled into and through ear canal 106. Disposed across the distal end of ear canal 106 is a tympanic membrane 104 which vibrates in response to acoustic wave 107. This vibration is coupled to oval window, or fenestra ovalis, 110 through three bones of middle ear 102, collectively referred to as the ossicles 111.

Ossicles 111 comprise malleus 112, incus 113 and stapes 114. Bones 112, 113 and 114 of middle ear 102 serve to filter and amplify acoustic wave 107, causing oval window 110 to articulate, or vibrate. Such vibration sets up waves of fluid motion within cochlea 115. Such fluid motion, in turn, activates tiny hair cells (not shown) that line the inside of cochlea 115. Activation of the hair cells causes appropriate nerve impulses to be transferred through the spiral ganglion cells (not shown) to auditory nerve 116 and, ultimately, to the brain where they are perceived as sound. In some persons experiencing sensorineural hearing loss, there is an absence or destruction of the hair cells. Cochlear implant 120 is utilized to directly stimulate the ganglion cells to provide a hearing sensation to such persons.

FIG. 1 also shows how cochlear implant 120 is positioned in relation to outer ear 101, middle ear 102 and inner ear 103. Cochlear implant 120 comprises external assembly 122 which is directly or indirectly attached to the body of the recipient, and an internal assembly 124 which is temporarily or permanently implanted in the recipient. External assembly 122 comprises microphone 125 for detecting sound which is provided to a behind-the-ear (BTE) speech processing unit 126 that generates coded signals. The coded signals are provided to an external transmitter unit 128, along with power from a power source (not shown) such as a battery. External transmitter unit 128 comprises an external coil 130 and, preferably, a magnet (not shown) secured directly or indirectly in external coil 130.

Internal assembly 124 comprises an internal receiver unit 132 having an internal coil (not shown) that transcutaneously receives power and coded signals from external assembly 122, and provides such signals to a stimulator unit 134. In response to the coded signals, stimulator 134 applies stimulation signals to cochlea 115 via an electrode assembly 140 implanted through temporal bone 160. Electrode assembly 140 enters cochlea 115 via an opening of the perilymphatic spaces of cochlea 115, referred to as cochleostomy 142, and has an array 144 of one or more electrodes 150 positioned to be substantially aligned with portions of tonotopically-mapped cochlea 115. The delivery of stimulation signals at various locations along cochlea 115 causes a hearing percept representative of the received sound 107.

Electrode assembly 140 preferably assumes an optimal electrode position in cochlea 115 upon or immediately following implantation into the cochlea. It is also desirable that electrode assembly 140 be configured such that the insertion process causes minimal trauma to the sensitive structures of cochlea 115. Typically, electrode assembly 140 is pre-curved, held in a substantially straight configuration at least during the initial stages of the implantation procedure, then conforming to the natural shape of the cochlea during, and subsequent to, implantation.

FIG. 2A is a functional block diagram of a cochlear implant 220 according to embodiments of the present invention in which internally-stored data from an implanted component 224 is transmitted (represented by the arrow) to an external component 222. In FIG. 2A, dashed line 290 represents the internal/external separation with regard to the recipient of the implant system 220 in which external component 222 is disposed outside of the recipient's body while implanted component 224 is disposed inside the recipient's body. As explained further below, the data transmitted from implanted component 224 to external component 222, in particular embodiments of the present invention, comprises programming data or other parameters specific to the recipient coded into memory or other data-retaining structure within implanted component 224. For example, data may be stored in any manner suitable for the particular application, including programmed in an application-specific integrated circuit (ASIC) or other computer hardware, software code, data tables stored in memory, etc.

While the precise details of speech processing schemes are not necessary for an understanding of the present invention, as a person having ordinary skill in the art will be aware, many processing schemes have been used and proposed. Virtually all such schemes rely on recipient-specific data. For example, following implantation it is usual for the implanted electrodes in a multi-electrode array to be tested for function, and for the sound percepts which are generated by stimuli to particular electrode pairs to be determined. These electrode-specific percepts are used in conjunction with a selected stimulation strategy to generate a recipient-specific "map". Even where two recipients use the same speech processing scheme, they may benefit from using different speech processing schemes and different parameters from one another. Further, each user may benefit from using a unique stimulus coding strategy. Other data may also be stored, for example alternative speech processing schemes and the user specific strategy for those schemes, or data of other types. All these data will be discussed as user specific parameters for the purposes of the discussion below, and are well understood by those skilled in the art.

In operation, when external component 222 is coupled to implanted component 224, recipient-specific data that is stored within implanted component 222 is transmitted (represented by the arrow) to memory within external component 222. External component 222 then uses the received data to program or configure external component 222 in order to operate in a manner dictated by the received recipient-specific data. Thus, external component 222 may be a generic yet compatible with implanted component 224, and not otherwise programmed or customized for the recipient prior to being coupled with implanted component 224. After being coupled with implanted component 224 and after downloading the recipient-specific parameters from implanted components 224, external component 222 will become non-generic as it becomes customized or otherwise programmed for the specific recipient from whose implanted component 224 the recipient-specific data was downloaded.

FIG. 2B is a functional block diagram of a cochlear implant 220 according to further embodiments of the present invention in which internally-stored data from implanted component 224 is transmitted (represented by the arrow) to an external component 222. In the embodiment illustrated, external component comprises an ambient sound pickup device or mic 225, an external processor 226, a power unit 227, an external memory module 228 and an external transmitter/receiver component 232. Implanted component 224 of the embodiment illustrated in FIG. 2B comprises an internal transmitter/receiver component 242, implanted processor 236, an implanted memory module 238 and a stimulation generator 241. Stimulation generator 241 is electrically coupled to an electrode array 244 which is configured to deliver electrical stimulation signals to hair cells in the cochlea of the recipient. As noted earlier, in the embodiment illustrated in FIG. 2B, recipient-specific parameter data is transferred from implanted memory module 238 via transmitters/receivers 232, 242 to external memory module 228 when external component 222 is brought into operational mode with implanted component 224, for example at startup or initialization. Furthermore, the hearing prosthesis may be configured such that the parameter data may be transferred from implanted memory module 238 to external memory module 228 periodically, for example every hour after the components 222, 224 are brought into an operational state. A portion of the periodically transferred data may comprise an ID code which is used to maintain continued operation of the hearing prosthesis as long as the received ID code matches the expected ID code.

By storing recipient-specific parameter data in implanted component 224 according to embodiments of the present invention, the recipient is able to replace external component 222, as long as external component 222 is compatible, without losing the recipient-specific parameter data which otherwise may stored in an external component as in conventional cochlear implants. Considering the time and therefore the cost to test and then fix a set of parameters fitted or customized to a particular recipient, and then to provide those parameters to the recipient's cochlear implant, one having skill in the art will appreciate the time and cost saved by storing those recipient-specific parameters within implanted component 224 and then downloading those parameters to one or many customizable but initially generic external component 222. Especially in the case of younger users of medical devices according to the present invention, the cost savings in providing a customizable but initially generic external component can be quite substantial. Furthermore, as external components advance in terms of design or functionality, the provider of the cochlear implant, for example the manufacturing of the external component for the cochlear implant, can simply provide the improved external component to the recipient, without having to provide for a programming process, who will be able to customize the replacement external component on their own according to embodiments of the present invention.

In one embodiment of the present invention, an ID code from implanted memory module 238 is transmitted from implanted component 224 to external component 222 during an initialization phase where external component 222 stores the ID code in memory 228. Later, during continued operation of the hearing prosthesis, the ID code from implanted memory module 238 is transmitted periodically from implanted component 224 to external component 222, where the received ID code is compared by processor 222 against the ID already stored in memory 228. Where the received ID code is identical to the ID code stored in memory 228, cochlear implant 220 continues operation. Where the received ID code is not identical to the ID code stored in memory 228, operation of cochlear implant 220 will halt and the device will enter into a fault or error state. Implanted component 224 is configured to wait a period of time during which the ID code. Where the ID code is not received during this window of time, or where the ID code received does not match the expected ID code, the implanted component 224 enters an error state. An indicator or alarm may be triggered from entering this fault or error state. In a further embodiment of the present invention, the ID code stored in memory 238 of implanted component 224 may be transmitted to and stored by external component 222 during initialization as described above. During operation, instead of implanted component 224 periodically transmitting the ID code, external component 222 periodically transmits the ID code to implanted code 224. Where processor 236 of implanted component 224 compares the received ID code to the ID code stored in memory 238 and finds them to be identical or otherwise acceptable, implanted component 224 continues operation. Where processor 236 finds the ID codes to not be identical, operations of cochlear implant 220 will halt or enter an error or fault state as described above.

FIGS. 2C and 2D illustrate different schemes for triggering the transfer of recipient-specific parameters. In FIG. 2C, a request (represented by the left-to-right arrow) for data is followed by a responsive download of the recipient-specific parameters, as will be understood by one having ordinary skill in the computer arts. FIG. 2D illustrates a different technique for triggering the data transfer in another embodiment of the invention in which an ID circuit 270, for example an RFID chip, is incorporated into external component 222. Implanted component 224 comprises a circuit configured to detect and received data from an ID circuit 270 such as an RFID chip. Upon detecting the ID circuit and upon passing a pre-programmed test, recipient-specific data stored in memory 238 of implanted component 224 is transmitted to external component 222 automatically. The pre-programmed test may be the matching of data representing a serial number or a model number. In one embodiment of the present invention, receiving a model number from ID 270 of external component 222 which is an exact match or within a range of acceptable model numbers stored in implanted component 222 will allow cochlear implant 220 to enter an operational state. Where the model number is not an exact match or within an expected range programmed into implanted component 224, hearing prosthesis will be prevented from entering an operational state, or if already in operational state, will cause hearing prosthesis to enter a fault or error mode.

It is to be understood that although the descriptions of the embodiments above describe the recipient-specific data being transferred from implanted component 224 to external component 222, the recipient-specific data may be transferred from external memory module 228 of external component 222 to implanted component 224 under embodiments of the present invention. In FIG. 3A, cochlear implant 320 comprises external component 322 and implanted component 324, with artificial dashed lined 390 indicating the division inside and outside the recipient's body. In the embodiment shown, data is transmitted (represented by the arrow) from external component 322 to implanted component 324. As detailed in FIG. 3B, in this particular embodiment of the present invention, data stored in an ID circuit 370, for example an RFID chip, is transmitted to implanted component 324. Upon verification of the data received from ID circuit 370, a functional component 327, for example a power pack, is able to transmit energy or data to implanted component 324. Where data received from ID circuit 370 is not verified or where the verification data fails to be received by implanted component 324, implanted component 324 may reject or otherwise not process data or other signal energy from external component 322. Functional component 327 may be one or more functional components including, but not limited to, a power module, a speech processor, amplification circuit, a DSP, among others. Data stored and transmitted from ID circuit 370 may comprise a serial number, encoded authentication data, a model number that is not unique to the particular device being coupled to implanted component 324, among other data. After the data is received from ID circuit 370, implanted processor 336 may conduct further processing, calculations or modifications of the received data in order to verify or authenticate the external component 322. One goal achieved by this particular embodiment of the present invention in which external component 322 is authenticated prior to being used with implanted component 324 is that strict manufacturing standards and quality control may be maintained in order to maximize safety for the recipient as well as to protect the public's perception of the manufacturer(s) of the authentic components.

Figure 4A:
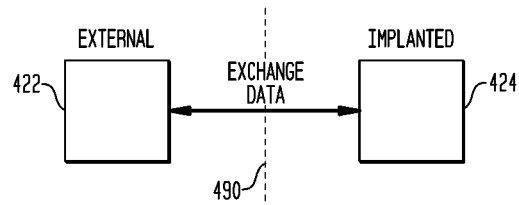
FIG. 4A is a functional block diagram of a cochlear implant according to embodiments of the present invention in which internally-stored recipient-specific operating parameters and externally stored data are exchanged between respective implanted and external components.
Figure 4B:
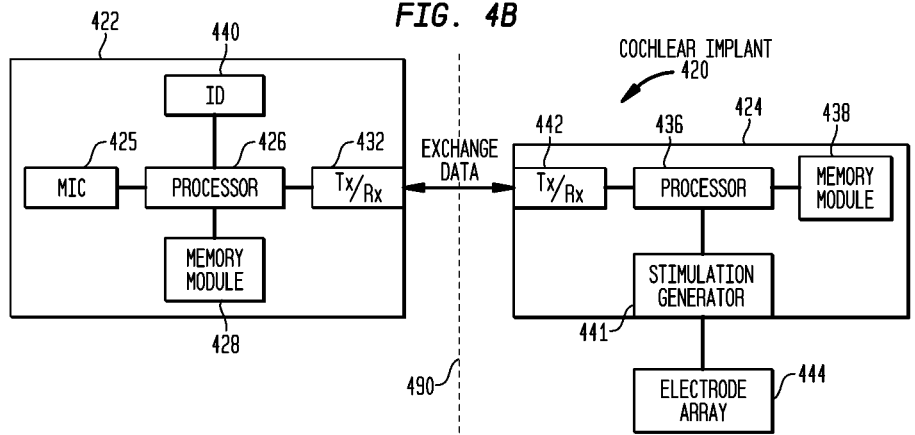
FIG. 4B is a functional block diagram of a cochlear implant according to embodiments of the present invention in which internally-stored recipient-specific operating parameters and externally stored data are exchanged between respective implanted and external components.

FIG. 4A is a functional block diagram of a cochlear implant 420 according to embodiments of the present invention in which internally-stored data and externally stored data are exchanged or communicated bi-directionally between respective implanted and external components 424 and 422. As shown in FIG. 4B, In this particular embodiment, authentication data may be stored in ID circuit 440. Upon authentication of external component 422 by implanted component 424 using authentication data from ID circuit 440, in a manner similar described above with respect to FIGS. 3A and 3B, implanted component 424 transmits recipient-specific data stored in implanted memory module 438, via implanted transmitter/receiver module 442 via external transmitter/receiver module 432 to processor 426. As described previously, upon receiving the recipient-specific data, external processor 426 configures various circuits and components of external component 422 managed by processor 426 to be customized for the recipient whose implanted component 424 transmitted the recipient-specific data. This embodiment of the present invention allows for both authentication of external component 422 using authentication data from ID circuit 440, as well as customization of external component 422 using recipient-specific data stored within implanted component 424.

Figure 5A:
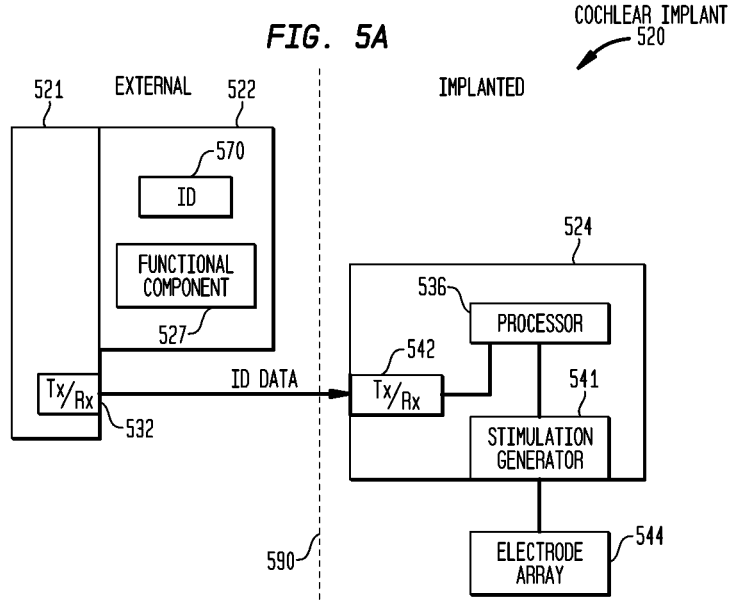
FIG. 5A is a functional block diagram of a cochlear implant according to embodiments of the present invention in which externally stored data is transmitted to an implanted component.
Figure 5B:
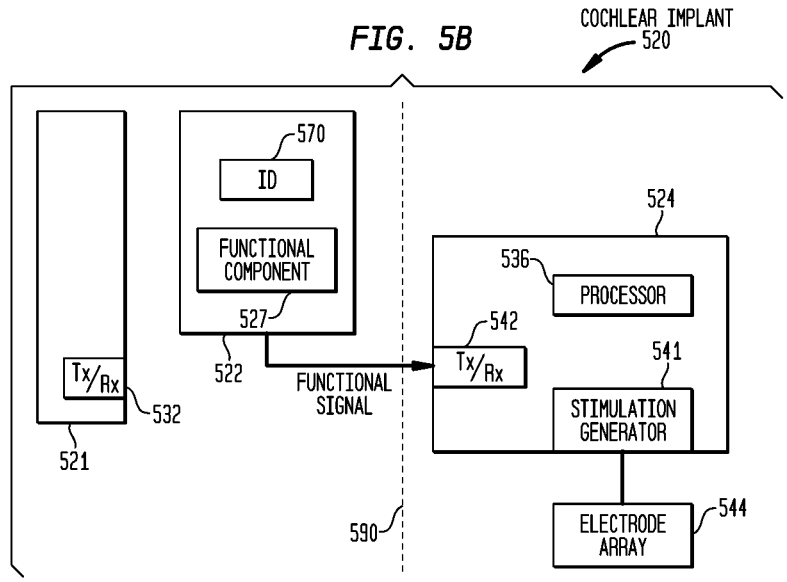
FIG. 5B is a functional block diagram of a cochlear implant according to other embodiments of the present invention in which externally stored data is transmitted to an implanted component.

FIG. 5A is a functional block diagram of a cochlear implant 520 according to embodiments of the present invention in which externally stored data is transmitted to an implanted component. As shown, external component 522 is coupled to a communication module 521 which retrieves or, in alternative embodiments of the present invention, receives authentication data from ID circuit 570. While external component 522 is coupled to communication module 521, external transmitter/receiver module 532 transmits retrieved (or received) authentication data via implanted transmitter/receiver module 542 to implanted processor 536 of implanted component 524. Following authentication by implanted component 524 of external component 522, as shown in FIG. 5B, communication module 521 is decoupled from external component 532 and data or energy from functional component 527 of external component 522 is transmitted and used by implanted component 524. In one particular embodiment of the present invention, functional component 527 may be a simple power module which is configured to transfer power through the housing (not shown) of external component 522 without a transmitter circuit or component. By providing a communication module 521 which may be decoupled following authentication or other data transfer, external component 522 may be configured to be smaller and simpler than if a communication component were to be incorporated into external component 522. As one having skill in the art will recognize, having a smaller and simpler external component may have many benefits for both the manufacturer as well as the recipient including reduced manufacturing cost, easier maintenance, allowing disposability of external component 522, lighter-weight body-worn external component 522, slimmer profile and overall aesthetics, among many others. Although FIGS.

5A and 5B are depicted with data being communicated only from external to implanted components 522, 524, it is to be understood that other embodiments of the present invention may be configured to allow bi-directional or implanted-to-external component communication of data.

Figure 6A:
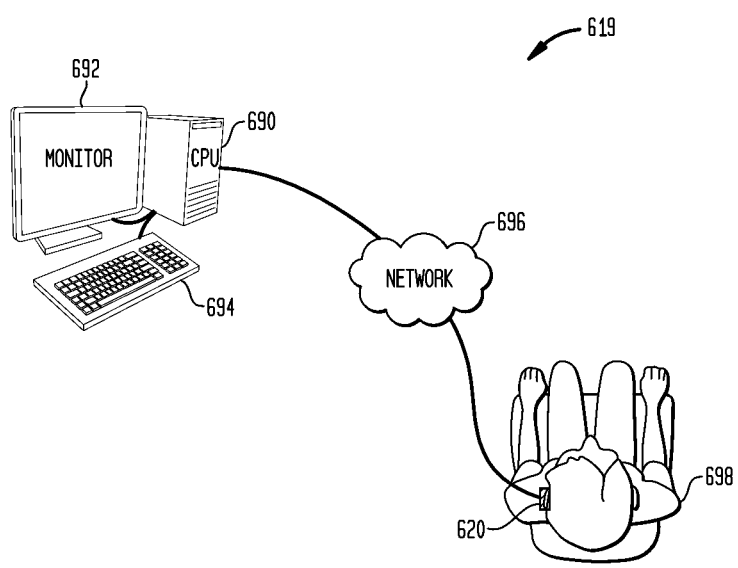
FIG. 6A is a schematic diagram of a cochlear implant programming system according to embodiments of the present invention.

FIG. 6A is a schematic diagram of a cochlear implant programming system 619 according to embodiments of the present invention. As depicted in FIG. 6A, a programming device, shown in FIG. 6A as a computer with CPU 690, display 692 and input device 694 shown as a computer keyboard, may be coupled via communication link 696 to the external component (not shown) of cochlear implant 620 in recipient 698. It is to be understood that the programming device shown as comprising CPU 690, display 692 and keyboard 694 may comprise different or additional components than is shown in FIG. 6A. Furthermore, it is to be understood that communication link 696 may comprise a local area network (LAN) including the association hardware and software, a wide area network (WAN) and the Internet, as well as any other intermediate communications channel, now known or later developed, which may enable communications between the programming system and cochlear implant 620 for recipient 698. Furthermore, although recipient 698 is illustrated as having recipient's cochlear implant 620 disposed within or on recipient 698, it is to be understood that other embodiments of the present invention will be configured to allow cochlear implant 620 to be programmed without participation by or in the presence of recipient 698.

In the embodiment illustrated in FIG. 6A, the cochlear implant 620 is provided with initial programming such that the initially-provided programming may be used as described above in order to customize an external component 522 (FIG. 5A) to be used with implanted component 524 (FIG. 5A). The provided initial programming may include recipient-specific parameters following one or more fitting sessions at the audiologist clinic.

FIG. 6B is a schematic diagram of an external and implantable components, 622 and 624 respectively, of a cochlear implant 620 according to embodiments of the present invention. As one of ordinary skill will appreciate, components 622 and 624 are greatly simplified for discussion purposes only. As described above, in one particular embodiment of the present invention, after implantation surgery and subsequent healing process, the recipient (not shown) may operationally couple external component 622 with implanted component 624. The recipient presses the "on" button of external component 622 or otherwise activates external component 622, which then causes external component 622 to retrieve recipient-specific data from implanted component 624. This retrieval by external component 622 of the recipient-specific data from implanted component 624 may be characterized by some having ordinary skill in the relevant art as "pulling" the data from implanted component 624 to external component 622.

In another embodiment of the present invention, the recipient pressing the "on" button of external component 622 or otherwise activating external component 622 causes external component 622 to broadcast an activation status signal which is received by implanted component 624. In response to receive the activation status signal, and not a data transmission request, implanted component 624 initiates a transmission of the recipient-specific data to the external component 622. This automatic initiation of the transmission of the recipient-specific data by and from implanted component 624 to external component 622 may be characterized by some having ordinary skill in the relevant art as "pushing" the recipient-specific data by implanted component 624 to external component 622.

In a further embodiment of the present invention, pressing the "on" button or otherwise activating (or allowing) external component 627 will trigger a transmission of authentication data from external component 622 to implanted component 624, which may be followed by a transmission of recipient-specific data from implanted component 624 to external component 622.

FIG. 7A is a flowchart diagram of the initial programming 700A of a cochlear implant according to embodiments of the present invention. In the embodiment illustrated, the implantable component is the "source" component from which data, such as recipient-specific parameters, is transferred to the external component. However, it is to be understood that in other embodiments of the present invention, including those described above, the "source" component may be the external component from which data, such as an ID code or other authentication data, may be transferred to the implanted memory module 338 (FIG. 3). As shown in block 710A, the source component is coupled to a cochlear implant programming system, such as programming system 619 (FIG. 6A) as described above. In block 720A, data is transferred from the programming system to the source component. The source component thus receives the transferred data from the programming system and acts as the "source" in later steps for one or more components which establishes a link to the source component.

FIG. 7B is a flowchart diagram of the initial programming 700B of a cochlear implant according to embodiments of the present invention. As noted above, the "source" component may be the implantable component in one embodiment of the present invention. In block 710B, the implantable component is coupled to a programming system, such as system 619 (FIG. 6A). In block 720B, the data is transferred to a memory module within the implantable component. In block 730B, the transferred data is verified as will be known to persons having skill in the relevant computer arts. After the data is transferred, in block 740B, the implantable component is de-coupled or otherwise disconnected from the programming system.

FIG. 7C is a flowchart diagram of the initial programming 700C of a cochlear implant described above with regard to FIG. 7B. The embodiment of the present invention illustrated in FIG. 7C is similar to the embodiment illustrated in FIG. 7B, but also comprises block 715C which, following the implantable component being coupled to the programming system, verifies the compatibility of the implantable component with the programming system. This verification may be accomplished in a variety of ways, in different embodiments of the present invention. In one embodiment of the present invention, ID code or other data such as serial number data, model number data, or other information found within a memory storage area of the implantable component may be retrieved by the programming system or otherwise transferred to the programming system. In other embodiments of the present invention, a proprietary physical connector and its unique dimensions is the verification mechanism, whereby the fact that an implantable component having one part of the proprietary connector is able to be physically connected the programming system which comprises the other part of the proprietary connector serves as the verification of compatibility in block 715C. Similar to the blocks described in conjunction with FIG. 7B, the programming data is transferred to the implanted memory module in block 720C, and then the transferred data is verified in block 730C. In block 740C, an INIT_DATA_ID variable is set by the programming system. The INIT_DATA_ID may comprise any data as long as it is sufficiently unique so as to be useful in verifying that the same implantable and external components coupled and activated are being used throughout the operation of the hearing prosthetic device. In one embodiment of the present invention, the programming system generates INIT_DATA_ID using date/time-stamp information from the programming system. In another embodiment of the present invention, INIT_DAT_ID is generated by an encryption program or circuit. In block 750C, the implantable device is decoupled from the programming system and is ready for implantation in or use by the recipient.

Where the "source" component is an implantable component rather than an external component, it is to be understood that the programming described above may occur in an implantable device which has not yet been implanted in the recipient. In one embodiment, the implantable component is programmed as described above during the manufacturing process. In another embodiment, the implantable component is programmed after being implanted in the recipient, either immediately upon implantation or after a period of time has passed. It is further to be understood that the "source" component may be an external component in other embodiments of the present invention.

FIG. 8A is a flowchart diagram of the programming 800A of a destination component from a source component of a cochlear implant according to embodiments of the present invention. In block 810A, the source component and the destination component are coupled to one another. In one embodiment of the present invention, the source component is an implantable component having an implanted memory module, as described above. In that embodiment, the destination component is an external component similarly comprising an external memory module. In another embodiment of the present invention, the source component is an external component and the destination component is an implantable component, each having respective memory modules from and to which data is transferred as described herein. In block 820A, data from the source component is transferred to the destination component. In block 830A, the cochlear implant, which comprises the implantable and external component, is operated using the data transferred between the source to destination components. In one embodiment of the present invention, the data transferred from the source component to the destination component is applied to the destination component such that the destination component becomes customized or otherwise modified to benefit the specific recipient. For example, where the destination component is an external speech processor component, the data transferred may comprise recipient-specific parameters, such as a map as described above, such that the speech processor component processes incoming audio signals and provides stimulation to the implantable component using the recipient's specific map.

FIG. 8B is a flowchart diagram of the programming 800B of a destination component from a source component of a cochlear implant according to other embodiments of the present invention. In block 805B, one or both of the implantable and external components verifies the compatibility of the components. In one embodiment of the present invention, this verification may be conducted through the detection or receipt of an ID code or other verifiable data from one of the implantable and external components. This verifiable data may comprise a serial number, a model number, a verification code, the combination of data sent in a specific and pre-determined sequence or manner, as well as other data or schemes now known or later developed useful in verifying one component to another. After the verification, a programming connection is established in block 810B between the source and destination components.

In one embodiment of the present invention, the destination component is the external component and the source component is the implantable component. In that embodiment of the present invention, the implantable and external component establishes a programming connection through, for example, a hand-shake sequence, as will be known to persons having skill in the relevant art. After the programming connection is established, data is transferred from the implantable component to the external component in block 820B. Once finished with the data transfer, the transferred data is verified in block 822B for accuracy, completeness, integrity, among other verifications. The data in INIT_DATA_ID is also transferred at block 824B from implantable component to the external component. The programming connection or session established at block 810B is terminated at block 826B when the programming is finished. Once the destination component has received the data, it is initialized or otherwise prepared at block 828B in one embodiment of the present invention. In one embodiment of the present invention, the data is copied or applied to the external component to modify the behavior of the external component during use of the overall cochlear implant by the recipient.

In block 830B, the external component is put in operational mode in block 830B. Periodically during use of the cochlear implant, at block 840B, the value stored in INIT_DATA_ID in the external component is compared to the INIT_DATA_ID from the source or implantable component. Where the values match or are otherwise acceptable with respect to one another, the cochlear implant is permitted to continue operations. Where the values differ, the cochlear implant enters an error state in block 850B. By thus periodically verifying the identify or acceptability of the external component, it will be possible to ensure that an unauthorized external component is not brought into operation with the implantable component. Furthermore, by also verifying compatibility of the external and implantable component at block 805B, it is possible to ensure that an unauthorized component is not used with the implantable component both initially and during normal operations.

Figure 9A:
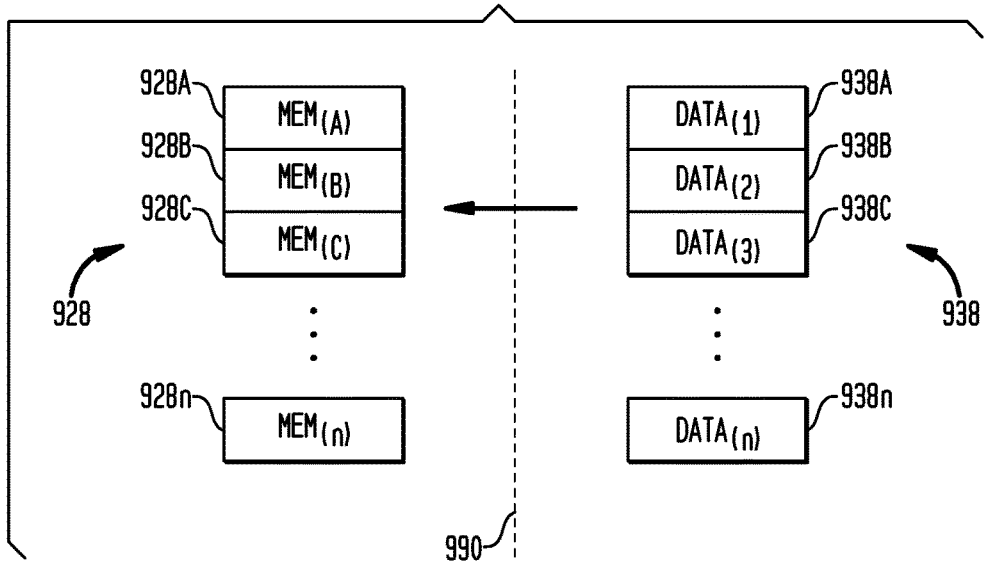
FIG. 9A is a schematic diagram of memory modules in implantable and external components of a cochlear implant according to embodiments of the present invention.

FIG. 9A is a schematic diagram of memory modules 928 and 938 respectively in implantable and external components of a cochlear implant according to embodiments of the present invention. In FIG. 9A, data is shown being transferred (represented by the arrow) from implantable memory module 938 to external memory module 928. However, it is to be understood that the data may be transferred from external memory module 928 to implantable memory module 938 in other embodiments of the present invention. In yet further embodiments of the present invention, the data is transferred both from and to each of memory modules 928, 938. As shown, the data in implantable memory module 938 comprises one or more data structures configured to receive and store one or more data. Also as shown in FIG. 9A, external memory module 928 comprises one or more data structures configured to receive and store one or more data.

Figure 9B:
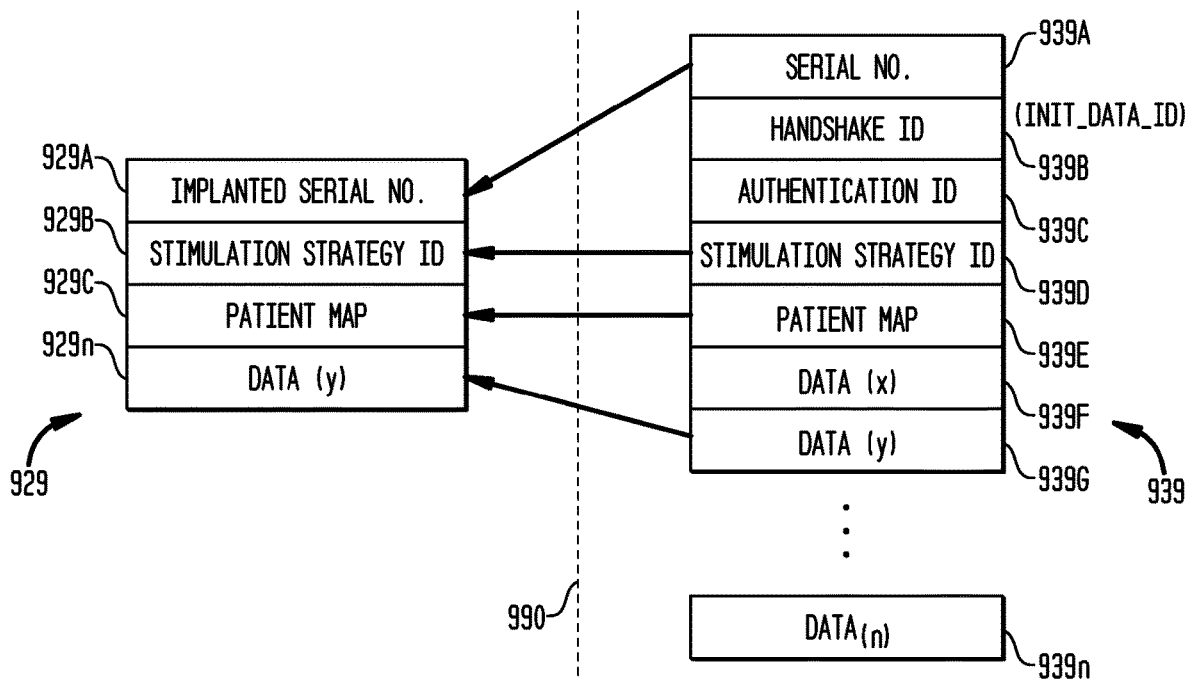
FIG. 9B is a schematic diagram of memory modules in implantable and external components of a cochlear implant according to further embodiments of the present invention.

Although external and implantable memory modules 928 and 938 are illustrated in FIG. 9A as being continuous, it is to be understood that the memory modules may comprise multiple physical components, each configured to receive and store, as well as transmit, one or more data. Additionally, as illustrated in FIG. 9B, it is to be understood that when data is transferred between external memory module 928 and implantable memory module 938, it is not necessary under embodiments of the present invention to transfer the entire data set contained therein. In certain embodiments, only a subset of data contained within the implantable memory module is transferred to the external memory module. In the particular embodiment illustrated in FIG. 9B, serial number 939A, stimulation strategy ID 939D, patient map 939E and data(y) 399G is transferred to external memory module 929.

As used herein, "electrical contact" and "electrode" have been used interchangeably. Furthermore, the term "comprising" (and its grammatical variations) as used herein is used in the inclusive sense of "having" or "including" and not in the exclusive sense of "consisting only of." The terms "a" and "the" as used herein are understood to encompass the plural as well as the singular. Also, "implantable components" and "implanted components" have been used interchangeably herein, referring to implantable component after being implanted in the recipient.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An implantable medical device comprising:
   an implantable component, comprising an implantable memory module, configured to receive and store recipient-specific operating parameters in said implantable memory module; and
   an external component, comprising an external memory module, configured to communicate with said implantable component to receive said recipient-specific operating parameters, and to be configured using said recipient-specific operating parameters,
   wherein said implantable medical device is configured to transfer said recipient-specific operating parameters upon operationally coupling said implantable component with said external component, and
   wherein said external component further comprises an identification circuit, said external component configured to transmit an identification code stored on said identification circuit, and
   further wherein said implantable component comprises a sensor configured to receive said identification code and further configured to transmit said recipient-specific operating parameters from said implantable memory module to said external memory module upon receiving said identification code.

2. The implantable medical device of claim 1, wherein said external component is configured to broadcast said identification code periodically.

3. The implantable medical device of claim 1, further comprising an external communication component configured to couple with said external component and to transmit said identification code from said external component to said implantable component, and further configured to receive and then provide said recipient-specific operating parameters from said implantable memory module to said external memory module.

4. The implantable medical device of claim 1, wherein said implantable component is configured to receive said identification code directly from said external component.

5. A method for programming an implantable medical device for a recipient having an implantable component and an external component, the components having a respective implantable memory module and external memory module, the method comprising:
   storing recipient-specific operating parameters in the implantable component;
   communicably coupling the implantable component and the external component;
   transferring the recipient-specific operating parameters from the implantable component to the external component; and
   configuring said external component by applying the recipient-specific operating parameters to the external component.

6. The method for programming an implantable medical device of claim 5, wherein said communicably coupling the implantable component to the external component further comprises:
   verifying the compatibility of the implantable component with the external component prior to said transferring recipient-specific operating parameters between the implantable memory module and the external memory module.

7. The method for programming an implantable medical device of claim 5, wherein said transferring recipient-specific operating parameters between the implantable memory module and the external memory module is via a wireless link between the implantable component and the external component.

8. The method for programming an implantable medical device of claim 5, wherein said transferring recipient-specific operating parameters between the implantable memory module and the external memory module comprises transferring a subset of data stored in the implantable memory module.

9. A non-transient computer readable medium comprising a computer program for controlling a processor to execute a method for configuring an implantable medical device for a recipient having an implantable component and an external component, the components respectively having an implantable memory module and external memory module, wherein the processor is disposed in the implantable component, the method comprising:
   storing recipient-specific operating parameters in the implantable component;
   communicably coupling the implantable component and the external component;
   transferring the recipient-specific operating parameters from the implantable component to the external component; and
   configuring said external component by applying the recipient-specific operating parameters to the external component.

10. The non-transient computer readable medium comprising a computer program for controlling a processor of claim 9, wherein said communicably coupling the implantable component to the external component further comprises:
    verifying the compatibility of the implantable component with the external component prior to said transferring recipient-specific operating parameters between the implantable memory module and the external memory module.

11. An implantable medical device for a recipient having an implantable component and an external component, the components having a respective implantable memory module and external memory module, the device comprising:
- means for storing recipient-specific operating parameters in the implantable component;
- means for communicably coupling the implantable component and the external component;
- means for transferring the recipient-specific operating parameters from the implantable component to the external component; and
- means for configuring said external component by applying the recipient-specific operating parameters to the external component.

12. The implantable medical device for programming an implantable medical device of claim 11, further comprising:
- means for verifying the compatibility of the implantable component with the external component prior to said transferring recipient-specific operating parameters between the implantable memory module and the external memory module.

13. An implantable medical device comprising:
- an implantable component, comprising an implantable memory module, configured to receive and store recipient-specific operating parameters in said implantable memory module; and
- an external component, comprising an external memory module, configured to communicate with said implantable component to transmit identification data to and to receive recipient-specific operating parameters from said implantable component,
- wherein said implantable medical device is configured to transfer said recipient-specific operating parameters upon operationally coupling said implantable component with said external component, and
- wherein said external component further comprises an identification circuit, said external component configured to transmit an identification code stored on said identification circuit, and further wherein said implantable component comprises a sensor configured to receive said identification code and further configured to enter an operational mode upon receiving said identification code.

14. The implantable medical device of claim 13, wherein said external component is configured to broadcast said identification code periodically.

15. The implantable medical device of claim 13, further comprising an external communication component configured to couple with said external component and to transmit said identification code from said external component to said implantable component.

16. The implantable medical device of claim 13, wherein said implantable component is configured to receive said identification code directly from said external component.

17. The implantable medical device of claim 13, said implantable component further configured to maintain said operational mode upon periodically receiving said identification code within a preset time period.

18. The implantable medical device of claim 13, wherein said external component further comprises a functional component configured to provide a functional signal to said implantable component.

19. The implantable medical device of claim 18, wherein said functional component is a power source.

20. The implantable medical device of claim 18, wherein said functional component is a speech processor.

21. The implantable medical device of claim 19, wherein said functional signal is a power signal from said power source.

22. The implantable medical device of claim 21, wherein said implantable component is configured to periodically match said received identification code from said external component to a corresponding identification code stored in said implantable memory module, and further configured to accept said power signal from said functional component only subsequent to said identification code being matched to said identification code.

* * * * *